US00PP21439P2

(12) United States Plant Patent
Trees et al.

(10) Patent No.: US PP21,439 P2
(45) Date of Patent: Nov. 2, 2010

(54) ***EUPHORBIA* PLANT NAMED 'BALBREWITE'**

(50) Latin Name: *Euphorbia hypericifolia*
Varietal Denomination: Balbrewite

(75) Inventors: Scott C. Trees, Arroyo Grande, CA (US); Tau-San Chou, Batavia, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/584,976

(22) Filed: Sep. 15, 2009

(51) Int. Cl.
*A01H 5/00* (2006.01)

(52) U.S. Cl. ..... Plt./302

(58) Field of Classification Search ..... Plt./302
See application file for complete search history.

*Primary Examiner*—Susan B McCormick Ewoldt
(74) *Attorney, Agent, or Firm*—Audrey Charles

(57) ABSTRACT

A new and distinct cultivar of *Euphorbia* plant named 'Balbrewite', characterized by its white-colored flower bracts, dark yellow-green colored foliage, and moderately vigorous, compact-mounded growth habit, is disclosed.

1 Drawing Sheet

Latin name of genus and species of plant claimed: *Euphorbia hypericifolia.*

Variety denomination: 'Balbrewite'.

BACKGROUND OF THE INVENTION

The present invention relates to a new and distinct cultivar of *Euphorbia* plant botanically known as *Euphorbia hypericifolia* and hereinafter referred to by the cultivar name 'Balbrewite'.

The new cultivar originated in a controlled breeding program in Arroyo Grande, Calif. during June 2006. The objective of the breeding program was the development of *Euphorbia* cultivars with continuous flowering, and a well-branched, compact-mounded growth habit.

The new *Euphorbia* cultivar was the result of a self-pollination followed by embryo rescue of Diamond Frost 'Inneuphdia', U.S. Plant Pat. No. 17,567, characterized by its white-colored flower bracts, dark yellow-green colored foliage, and compact, upright and outwardly spreading growth habit. The new cultivar was discovered and selected as a single flowering plant within the progeny of the above stated self-pollination and embryo rescue during December 2006 in a controlled environment at Arroyo Grande, Calif.

Asexual reproduction of the new cultivar by terminal stem cuttings since December 2006 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balbrewite' as a new and distinct cultivar of *Euphorbia* plant:

1. White-colored flower bracts;
2. Dark yellow-green colored foliage; and
3. Moderately vigorous, compact-mounded growth habit.

Of the many commercially available *Euphorbia* cultivars, the most similar in comparison to the new cultivar is the parent Diamond Frost 'Inneuphdia', U.S. Plant Pa. No. 17,567. However, in a side by side comparison conducted in West Chicago, Ill., plants of the new cultivar were shown to have more inflorescences than plants of 'Inneuphdia'. The new cultivar had approximately 100 inflorescences per plant while those of the parent had approximately 60 inflorescences per plant.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balbrewite'. The plants were grown in 4.5 inch pots for 7 weeks in a greenhouse at West Chicago, Ill.

DETAILED BOTANICAL DESCRIPTION

Figure 1:
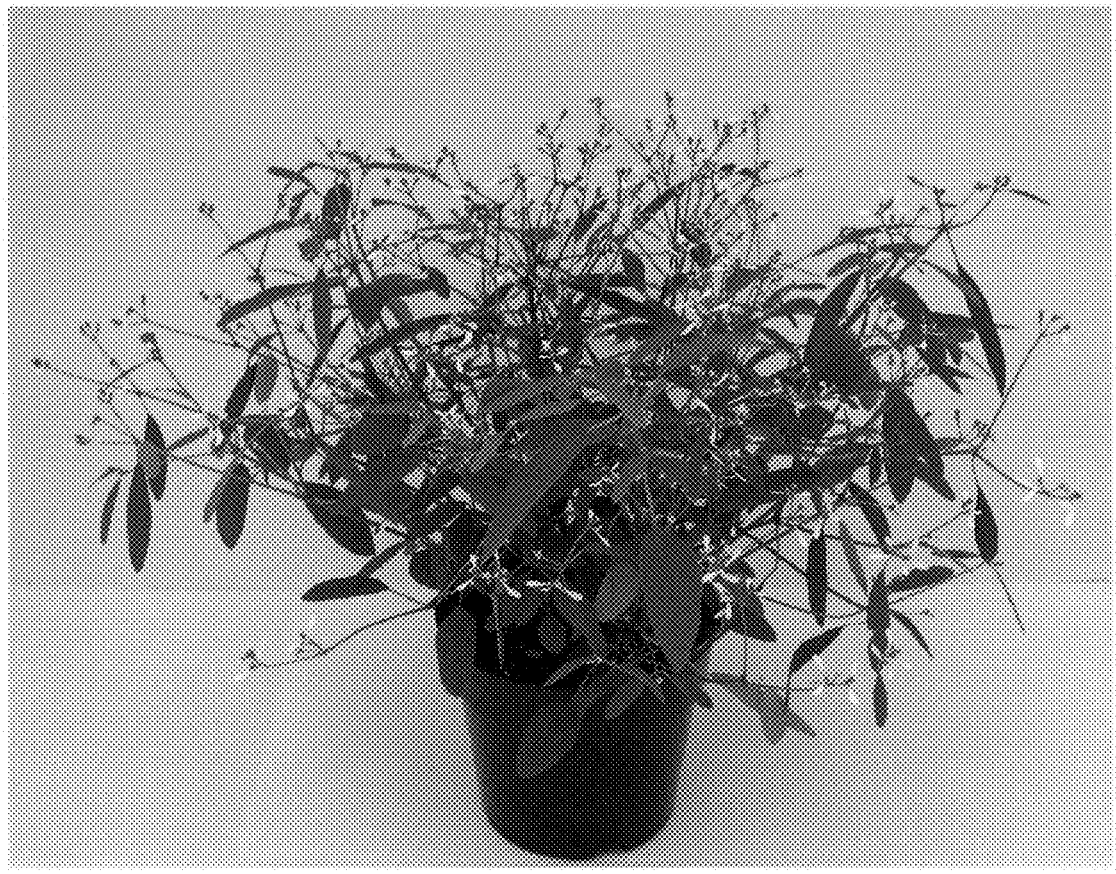
FIG. 1 illustrates a side view of the overall growth and flowering habit of 'Balbrewite'.
Figure 2:
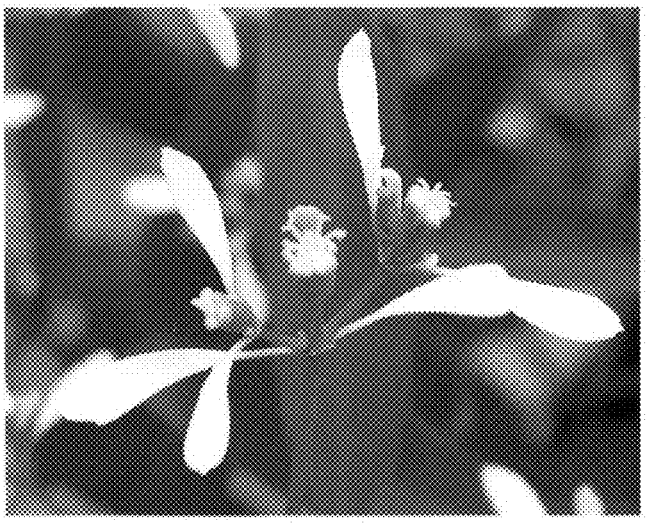
FIG. 2 illustrates a close-up view of an individual inflorescence of 'Balbrewite'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in August 2009 under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 7 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Euphorbia hypericifolia* cultivar Balbrewite.

Parentage:

*Female and male parents.*—Diamond Frost 'Inneuphdia', U.S. Plant Pat. No. 17,567.

Propagation:

*Type cutting.*—Terminal stem.

*Time to initiate roots.*—Approximately 14 to 18 days.

*Time to produce a rooted cutting.*—Approximately 21 to 28 days.

*Root description.*—Fine, fibrous, white in color.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, compact and mounded.

*Size.*—Height from soil level to top of plant plane: Approximately 24.7 cm. Width: Approximately 36.0 cm.

*Branching habit.*—Freely branching with numerous secondary and tertiary branching. Pinching improves basal branching. Quantity of main branches per plant: Approximately 6.

*Branch.*—Shape: Round in cross section. Strength: Strong. Length: Approximately 24.9 cm. Diameter: Approximately 3.0 mm. Length of central internode: Approximately 4.4 cm. Texture: Smooth, glabrous. Color of young stem: 146A. Color of mature stem: 146A with an overlay of 187A at nodes.

Foliage description:

*General description.*—Quantity of leaves per main branch: Approximately 8. Fragrance: None. Form: Simple. Arrangement: Opposite.

*Leaves.*—Shape: Elliptical. Margin: Entire. Apex: Acute. Base: Attenuate. Venation pattern: Pinnate, arcuate. Length of mature leaf: Approximately 4.9 cm. Width of mature leaf: Approximately 1.5 cm. Texture of upper and lower surfaces: Sparsely pubescent. Color of upper surface of young foliage: 146A with indistinguishable venation. Color of lower surface of young foliage: 146B with midveins of 146C. Color of upper surface of mature foliage: 147A with indistinguishable venation. Color of lower surface of mature foliage: 147B with midveins of 147C.

*Petiole.*—Length: Approximately 2.1 cm. Diameter: Approximately 1.0 mm. Texture: Sparsely pubescent. Color: 146A with a faint overlay of 187A nearest stem.

Flowering description:

*Flowering habit.*—'Balbrewite' is freely flowering under outdoor growing conditions with substantially continuous blooming from spring through autumn and year-round in greenhouse environment.

*Lastingness of individual flower on the plant.*—Approximately 10 days.

Inflorescence description:

*General description.*—Type: Compound terminal cymes. Quantity per plant: Approximately 100. Fragrance: None. Length (height): Approximately 1.7 cm. Width: Approximately 3.0 cm. Quantity of fully open flowers per inflorescence: Approximately 3.

*Peduncle.*—Shape: Round in cross section. Strength: Strong, flexible. Aspect: Vertical or 45° angle to stem. Length: Approximately 5.0 cm. Diameter: Approximately 1.0 mm. Texture: Smooth, glabrous. Color: 146A.

Flower description:

*Type.*—Cyathia, persistent.

*Bud.*—Quantity per inflorescence: Approximately 2.

*Bud just before opening.*—Shape: Ovoid. Length: Approximately 2.0 mm. Width: Approximately 1.5 mm. Texture: Smooth, glabrous. Color: 143A.

*Cyathia.*—Shape: Cup-shaped. Length: Approximately 5.5 mm. Width: Approximately 2.0 mm. Texture: Smooth, glabrous. Color: 143A.

*Floral bracts.*—Quantity: 2, opposite. Shape: Elliptical to lanceolate. Appearance: Dull. Margin: Entire. Apex: Rounded to acute. Base: Attenuate. Length: Approximately 1.0 cm. Width: Approximately 2.0 mm. Texture of upper and lower surfaces: Glabrous, smooth. Color of upper and lower surfaces: Purer white than 155D.

*Nectaries.*—Quantity: 4 at rim of cyathium. Shape: Ovoid With lunate petaloid appendage. Length: Approximately 1.0 mm. Width: Approximately 1.0 mm. Color: 143A with purer white than 155D at petaloid apex.

*Cyathia pedicels.*—Strength: Strong. Aspect: Erect or approximately 45° from vertical. Length: Approximately 4.0 mm. Diameter: Less than 1 mm. Texture: Smooth, glabrous. Color: 146B.

*Reproductive organs.*—Androecium: Stamen quantity: 3 to 4 fully developed per cyathium. Stamen length: Approximately 4.0 mm. Filament color:

Colorless, transparent. Anther shape: Bilobed. Anther length: Less than 1 mm. Anther color: 158C with a central area of 187A. Pollen amount: Scarce. Pollen color: 158D. Gynoecium: Pistil quantity: 1 per cyathium. Pistil length: Approximately 2.0 mm to 3.0 mm to base of ovary; base of ovary is attached to a stalk that can expand to 3.0 mm in a fully mature cyathium. Stigma shape: 6 parted. Stigma length: Less than 1 mm. Stigma color: 155D. Style length: Approximately 1.0 mm. Style color: 155D. Ovary diameter: Approximately 1.0 mm. Ovary color: 143A. Stalk color: Colorless, transparent.

Seed and fruit production: Neither seed nor fruit production has been observed.

Disease and pest resistance: Resistance to pathogens and pests common to *Euphorbia* has not been observed.

What is claimed is:

1. A new and distinct cultivar of *Euphorbia* plant named 'Balbrewite', substantially as herein shown and described.

* * * * *